United States Patent

Harms et al.

[11] Patent Number: 6,106,526
[45] Date of Patent: *Aug. 22, 2000

[54] MEMBER FOR STABILIZING CERVICAL VERTEBRAE

[76] Inventors: Jürgen Harms, Vogesenstr. 60, 76337 Waldbronn; Lutz Biedermann, Am Schäfersteig 8, 78048 VS-Villingen, both of Germany

[*] Notice: This patent issued on a continued prosecution application filed under 37 CFR 1.53(d), and is subject to the twenty year patent term provisions of 35 U.S.C. 154(a)(2).

[21] Appl. No.: 08/737,156
[22] PCT Filed: Mar. 1, 1996
[86] PCT No.: PCT/EP96/00883
  § 371 Date: Nov. 8, 1996
  § 102(e) Date: Nov. 8, 1996
[87] PCT Pub. No.: WO96/28105
  PCT Pub. Date: Sep. 19, 1996

[30] Foreign Application Priority Data

Mar. 15, 1995 [DE] Germany ............ 195 09 331

[51] Int. Cl.[7] .................................................. A61B 17/70
[52] U.S. Cl. .................................. 606/61; 606/69
[58] Field of Search .................. 606/61, 60, 72, 606/73, 69, 70, 71

[56] References Cited

U.S. PATENT DOCUMENTS 5,261,912 11/1993 Frigg .......................................... 606/61
5,312,404  5/1994 Asher et al. ............................... 606/61
5,360,429 11/1994 Jeanson et al. ........................... 606/61

FOREIGN PATENT DOCUMENTS 39 23 995 C2  1/1991 Germany .
WO 92/03100  3/1992 WIPO .
WO 94/26194 11/1994 WIPO .

Primary Examiner—Guy V. Tucker
Attorney, Agent, or Firm—George W. Neuner

[57] ABSTRACT

A member for stabilizing cervical vertebrae is provided with a body 1 with a plate-shaped portion having a bore 2 extending perpendicular to the plane plate, and a bone screw 3 having a threaded portion 4 and a head 5, whereby the threaded portion 4 extends through the bore. In order to provide a member usable for stabilizing the cervical spinal column the member has, in a second portion 9 which is laterally offset with respect to the bore in the plate plane, an external screw thread 10 and a slit 11 extending in direction of the thread axis for receiving a fastening rod 12 for the support thereof. Moreover, a nut 13 cooperating with the external screw thread 10 for locking the rod 12 to be inserted is provided.

5 Claims, 1 Drawing Sheet

MEMBER FOR STABILIZING CERVICAL VERTEBRAE

This application is a 371 application of PCT/EP96/00883 filed Mar. 1, 1996.

BACKGROUND OF THE INVENTION

The invention relates to a member for stabilizing cervical vertebrae.

The German patent 39 23 995 discloses a stabilizing member for stabilizing cervical vertebrae. This member comprises a plate, which is bent to adapt it to the desired shape of the cervical spinal column. Thereafter, a plurality of bolts are screwed into the individual adjacent vertebrae. If the surgeon determines that the bending line is not perfect or must be changed for medical reasons, all screws must again be unscrewed in order to rebend the plate. This should be followed by again screwing in the bolts; For stability reasons of the vertebrae such a renewed screwing operation is hardly possible because of the weak anchoring in the bone so that in practice it must be done without such a later correcting alignment. The U.S. Pat. No. 5,312,404 discloses a member for stabilizing vertebrae which comprise a body with a plate-shaped portion and a bore extending perpendicular to the plane of the plate. A bone screw with a threaded portion and a head is provided, whereby the threaded portion extends through the bore towards a first side of the plane of the plate and the head of a bone screw is supported by the plate-shaped portion. The member has a second portion which is laterally offset with respect to the bore in the plane of the plate adjacent to the plate-shaped portion. The second portion comprises a bore for receiving a rod. A threaded bore for receiving a screw is provided perpendicular to the axis of this bore. The rod is fixed by means of a screw screwed into this threaded bore.

The U.S. Pat. No. 5,360,429 discloses a member for stabilizing vertebrae which consists of a body with a plate-shaped portion and a laterally offset second portion. The second portion comprises a slit which is provided with an external screw thread and serves for receiving a rod to be supported therein. A nut cooperating with the external screw thread serves for locking the rod to be placed therein.

It is the object of the invention to provide a member for stabilizing cervical vertebrae wherein the rod to be received is permanently locked.

This object is achieved by the member for stabilizing cervical vertebrae characterized in claim 1. Further developments of the invention are characterized in the subclaims.

BRIEF DESCRIPTION OF THE DRAWINGS

Further features and advantages of the invention will be apparent from the description of an embodiment with reference to the Figures. In the Figures.

DETAILED DESCRIPTION OF THE INVENTION

Figure 1:
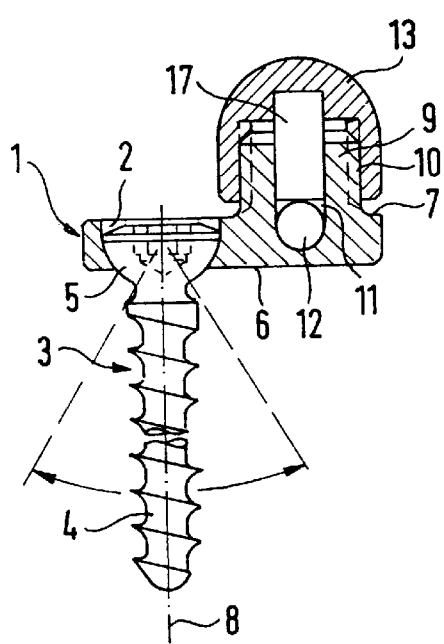
FIG. 1 is an enlarged sectional view along line I—I of FIG. 2.
Figure 2:
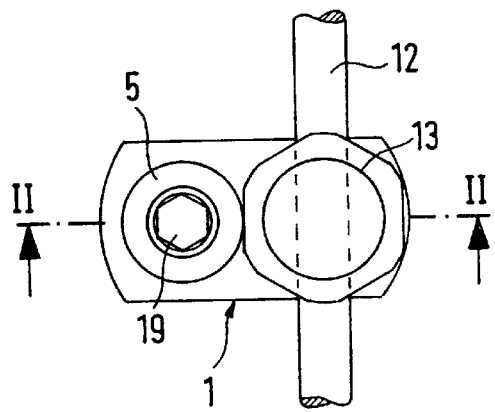
FIG. 2 is a top view of the member shown in FIG. 1.

As best shown in the FIGS. 1 and 2 the member comprises a plate-shaped body 1 which has a substantially rectangular form.

The body has a bore 2 which is provided about centrally in one half thereof and aligned perpendicular to the plane of the plate. A bone screw comprising a threaded portion 4 and a head 5, as for example known from the cited German patent 39 23 995, is disposed in the bore 2. The threaded portion 4 extends through the bore in direction of the first side 6 of the plate-shaped body 1. The bore has an edge portion formed as a spherical segment shaped recess at the second side 7 of the plate-shaped body opposite to the first side 6. The head 5 has a corresponding convex spherical segment shape at its lower side facing the threaded portion 4. The radius of the spherical segment shaped recess and of the corresponding convex spherical segment shaped portion of the spherical segment shaped head are substantially equal and match each other so that the bone screw can pivot around the axis 8 within the conical region indicated by the dotted lines for conveniently screwing the bone screw into the vertebrae.

The second half of the body comprises a cylindrical projection 9 extending towards the second side 7. The cylindrical projection 9 comprises an external screw thread 10. Its symmetry or thread axis, respectively, extends perpendicular to the plate plane of the body 1 and parallel to the axis of bore 2, respectively.

As best shown in FIG. 1 a U-shaped slit 11 extends along a plane of symmetry containing the axis of symmetry of the cylindrical projection 9. The slit 11 comprises two lateral walls which are parallel to the axis of symmetry, and a slit base shaped substantially as a cylinder portion. The slit serves to receive a fastening rod 12. The slit and its base are sized to allow the introduction of the fastening rod 12 into the slit and down to the base thereof without the rod having a lateral clearance.

Figure 3:
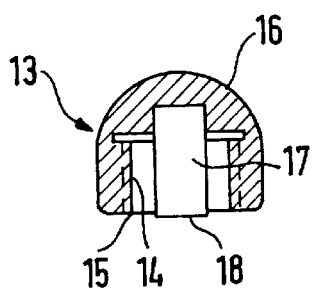
FIG. 3 is a side view of a part of the member shown in the FIGS. 1 and 2.

Moreover, a nut 13 is provided which, as best shown in FIG. 3, has a portion comprising an internal screw thread 14 adjacent to the rim 15. The nut has a domed cap 16 at its end opposite to the rim 15. The cap has a coaxially aligned pressure pin 17 provided at its side facing the internally threaded portion. The pressure pin 17 is sized so that its free end projects beyond the rim 15 of the nut 13 by fractions of a millimeter. The diameter of the pin is equal to or slightly smaller than the diameter of the rod 12 so that the pin, on the one hand, can be freely introduced into the slit 11 and, on the other hand, is laterally guided by the slit.

The internal screw thread 14 is adapted to cooperate with the external screw thread 10 of the cylindrical projection 9. The length of the internal screw thread 14 exceeds, dependent on the axial length of the cylindrical projection 9 and of the depth of the slit 11, the depth of the slit minus the diameter of the rod 12 to be placed therein.

As best shown in FIG. 2 the bone screw 3 has a hexagon bore 19 at its side opposite to its threaded portion 4 for screwing-in the screw by means of a screw driver.

In operation first respective bodies of the above-described type are screwed into adjacent vertebrae by means of bone screws 3 which are not yet tightened to their final position. Thereafter, the fastening rod 12 is introduced into the respective slit of the adjacent bodies. Then the cap nut 13 is screwed on whereby the position of the fastening rod 12 is fixed by the slightly projecting pressure pin 17 even before finally tightening the nut. In case of a desired modification merely the nut is again loosened, the rod is removed and rebend, again inserted and thereafter held by the pressure pins by screwing-on the nuts.

After obtaining the final adjustment the bone screw 3 is tightened and a final lock is obtained by tightening the nut 13. An unreleasable lock is obtained by cooperation of the nut 13 and the pressure pin abutting the inner walls of the U-shaped slit.

The above-described design allows a correctable adjustment and fixation of the adjusted vertebrae to be obtained even in the region of the cervical spinal column where there is very restricted room for mounting a fixation device.

We claim:

1. A member for stabilizing cervical vertebrae, comprising:

a body member having a plate-shaped first portion and a second portion, said first portion extending substantially in a plane of said plate and having a lower first side and an upper second side, a bore extending through said first portion in a direction substantially perpendicular to said plane, said second portion being laterally offset with respect to said bore in said plane, means projecting from said plane in said second portion and having external thread means with a thread axis and slit means extending in direction of said thread axis for receiving a fastening rod, said slit means being defined by opposite lateral walls of said projecting means, domed-cap nut means having a continuous exterior surface, an interior surface separated from said exterior surface without a throughhole connecting the interior and exterior surfaces, and internal thread means cooperating with said external thread means, a pressure pin having a first end and second end, said first end abutting said interior surface of said domed-cap nut means and said second end extending into said slit means while being guided by said lateral walls to lock a fastening rod inserted into said slit means when tightening said nut means, and a bone screw having a threaded portion and a head, said head being supported by said first portion of said body member and said threaded portion extending through said bore towards and from said lower first side of said first portion.

2. The member of claim 1, wherein said nut means has a rim facing said plane and said pressure pin projects outwardly beyond said rim.

3. The member of claim 1, wherein said bore has an edge formed as a spherical segment shaped recess provided at the end of the bore joining said upper second side of said first portion, and said head comprises a corresponding convex spherical segment shaped portion at its side facing said threaded portion.

4. The member of claim 1, wherein said nut means and said pressure pin are formed as one piece.

5. The member of claim 1, wherein said thread axis extends perpendicular to said plane.

* * * * *

UNITED STATES PATENT AND TRADEMARK OFFICE
CERTIFICATE OF CORRECTION

PATENT NO. : 6,106,526
DATED : August 22, 2000
INVENTOR(S) : Jurgen Harms and Lutz Biedermann It is certified that error appears in the above-identified patent and that said Letters Patent is hereby corrected as shown below:

Title page,

In the Foreign Application Priority Data section, please correct the priority data as follows:

[30]  Foreign Application Priority Data

GERMANY, MARCH 15, 1995, 195 09 331.3

Signed and Sealed this

Twenty-fourth Day of April, 2001

Attest:

NICHOLAS P. GODICI

*Attesting Officer*    *Acting Director of the United States Patent and Trademark Office*